United States Patent [19]

Tong et al.

[11] Patent Number: 5,779,881
[45] Date of Patent: Jul. 14, 1998

[54] PHOSPHONATE/THIOPHOSPHONATE COKING INHIBITORS

[75] Inventors: Youdong Tong, Houston; Michael K. Poindexter, Sugar Land, both of Tex.

[73] Assignee: Nalco/Exxon Energy Chemicals, L.P., Sugar Land, Tex.

[21] Appl. No.: 778,995

[22] Filed: Jan. 6, 1997

Related U.S. Application Data

[63] Continuation-in-part of Ser. No. 343,059, Nov. 21, 1994, abandoned, which is a continuation-in-part of Ser. No. 190,954, Feb. 3, 1994, abandoned.

[51] Int. Cl.$^6$ ..................................................... C10G 9/12
[52] U.S. Cl. .................. 208/48 AA; 585/950; 208/48 R
[58] Field of Search ............................................. 585/950

[56] References Cited

U.S. PATENT DOCUMENTS

| | | |
|---|---|---|
| 3,531,394 | 9/1970 | Koszman . |
| 3,837,803 | 9/1974 | Carter et al. . |
| 3,951,837 | 4/1976 | Sheratte . |
| 3,957,668 | 5/1976 | Sheratte . |
| 4,105,540 | 8/1978 | Weinland . |
| 4,303,568 | 12/1981 | May et al. . |
| 4,451,442 | 5/1984 | Jeffrey et al. . |
| 4,542,253 | 9/1985 | Kaplan et al. . |
| 4,828,674 | 5/1989 | Forester . |
| 4,830,838 | 5/1989 | Kent et al. . |
| 4,835,332 | 5/1989 | Kisalus . |
| 4,842,716 | 6/1989 | Kaplan et al. . |
| 4,900,426 | 2/1990 | Kisalus . |
| 4,927,519 | 5/1990 | Forester . |
| 5,354,450 | 10/1994 | Tong et al. . |
| 5,360,531 | 11/1994 | Tong et al. . |

*Primary Examiner*—Helane Myers
*Attorney, Agent, or Firm*—Tom M. Breininger; Kelly L. Cummings

[57] ABSTRACT

A method to inhibit coke formation on heat transfer surfaces used to heat or cool a petroleum feedstock at coke-forming conditions is disclosed. The heat transfer surfaces are treated with an effective amount of phosphonate to inhibit coke formation on the heat transfer surfaces. The phosphonate is essentially free from contributing to corrosion and from producing detrimental by-products.

14 Claims, 2 Drawing Sheets

PHOSPHONATE/THIOPHOSPHONATE COKING INHIBITORS

The present application is a continuation-in-part of application Ser. No. 08/343,059 filed Nov. 21, 1994 entitled "Phosphonate/Thiophosphonate Coking Inhibitors", now abandoned, which is, in turn, a continuation-in-part of application Ser. No. 08/190,954 filed Feb. 3, 1994, now abandoned, entitled "Phosphonate/Phosphothionate Coking Inhibitors", the disclosures of which are incorporated herein by reference.

FIELD OF THE INVENTION

The invention relates to an antifouling process for treating heat transfer surfaces which heat or cool various hydrocarbon feedstocks, often in the presence of steam, at conditions tending to promote the formation of coke on the surfaces, and more particularly, to phosphonates/thiophosphonates for use as antifoulants.

BACKGROUND OF THE INVENTION

Ethylene manufacture entails the use of pyrolysis or cracking furnaces to manufacture ethylene from various gaseous and liquid petroleum feedstocks. Typical gaseous feedstocks include ethane, propane, butane and mixtures thereof. Typical liquid feedstocks include naphthas, kerosene, and atmospheric/vacuum gas oil. When gaseous or liquid hydrocarbon feedstocks are pyrolyzed in the presence of steam, significant quantities of ethylene and other useful unsaturated compounds are obtained. Steam is used to regulate the cracking reaction of saturated feedstocks to unsaturated products. The effluent products are quenched and fractionated in downstream columns, and then further reacted or processed depending on need.

Fouling of cracking furnace coils, transfer line exchangers (TLEs) and other heat transfer surfaces occurs because of coking and polymer deposition. The fouling problem is one of the major operational limitations experienced in running an ethylene plant. Depending on deposition rate, ethylene furnaces must be periodically shut down for cleaning. In addition to periodic cleaning, crash shutdowns are sometimes required because of dangerous increases in pressure or temperatures resulting from deposit buildup in the furnace coils and TLEs. Cleaning operations are carried out either mechanically or by passing steam and/or air through the coils to oxidize and burn off the coke buildup.

A major limitation of ethylene furnace run length is coke formation in the radiant section and transfer line exchangers (TLEs). The coke is normally removed by introducing steam and/or air to the unit, which in effect burns off carbonaceous deposits. Since coke is a good thermal insulator, the furnace firing must be gradually increased to provide enough heat transfer to maintain the desired conversion level. Higher temperatures shorten the tube life, and tubes are quite expensive to replace. Additionally, coke formation decreases the effective cross-sectional area of the process gas, which increases the pressure drop across the furnace and TLEs. Not only is valuable production time lost during the decoking operation, but also the pressure buildup resulting from coke formation adversely affects ethylene yield. Run lengths for ethylene furnaces average from one week to four months depending in part upon the rate of fouling of the furnace coils and TLEs. This fouling rate is, in turn, dependent upon the nature of the feedstock as well as upon furnace design and operational parameters. In general, however, heavier feedstocks and higher cracking severity results in an increased rate of furnace and TLE fouling. A process or additive that could increase run length would lead to fewer days lost to decoking and lower maintenance costs.

Significant effort has been exerted over the past twenty years in developing phosphorus, in numerous forms, as a coke inhibitor. See U.S. Pat. Nos. 3,531,394 to Koszman (phosphoric acid); 4,105,540 to Weinland (phosphate and phosphite mono and diesters); 4,542,253 and 4,842,716 to Kaplan et al. (amine complexes of phosphate, phosphite, thiophosphate and thiophosphite mono and diesters); 4,835, 332 to Kisalus (triphenyl phosphine); and 4,900,426 to Kisalus (triphenyl phosphine oxide). Compared with other element-based additives, many of these phosphorus-based antifoulants have performed extremely well with respect to coke suppression in both lab simulations and industrial applications. However, some have yielded detrimental side effects preventing prolonged usage in many situations, e.g., contributing to corrosion, and impairing catalyst performance, among others.

Convection section corrosion has been a problem with many known phosphorus-based anticoking additives. Along the path of the convection section tubing, conditions are constantly changing. Heated steam and hydrocarbon are typically introduced to the section separately and then mixed well before entering the radiant section. During the numerous passes that the streams experience, either separated or mixed, temperatures, pressures, and compositions may exist which enhance the conversion of antifoulants to detrimental corrosive by-products. A product which is an excellent coke suppressant may also be an extremely corrosive species if it accumulates in the convection section.

Once additives pass through the convection, radiant, and TLE sections, they are subject to effluent quench conditions. In a very simplified view, heavy products concentrate in the primary fractionator, water quench tower, caustic tower and/or compressor knock-out drums, while the lighter components are collected in columns downstream of the compressors. Accumulation of coke inhibitors and their cracked by-products is dictated mainly by their physical properties. Briefly, inhibitor by-products with high boiling points are condensed early in the fractionation process while lighter ones progress to the later stages.

Additives and/or by-products that go past the caustic tower and compressor sections can be a significant problem. Past these sections, purity becomes an important issue since the downstream fractionation generally separates the unsaturated products into high purity chemicals. The presence of phosphorus-containing products which might adversely affect the performance of catalysts used to process these lighter components and the final products, e.g., polymer grade ethylene, is unacceptable.

Accordingly, there remains a need for a phosphorus-based anticoking additive for cracking furnaces which is essentially free from contributing to corrosion and from forming downstream contamination by-products.

SUMMARY OF THE INVENTION

The present invention discloses a method for the use of a new antifoulant and coke suppressant, dihydrocarbon (i.e., di-alkyl,-alkylaryl,-aryl, or arylalkyl) hydrocarbon (i.e., alkyl, alkylaryl, aryl or arylalkyl) phosphonates/ thiophosphonates, (hereafter referred to as phosphonates) to reduce fouling in various high temperature applications, including steam cracking furnaces. These phosphonates have the formula of $(R'Y)_2P(X)R''$, wherein X and Y are chalcogens, preferably oxygen or sulfur, and wherein R'=alkyl, alkylaryl, aryl, arylalkyl or heteroatom-containing substituents with the proviso that the heteroatom of said heteroatom-containing substituent is not directly bonded to the phosphorous atom and R"=alkyl, arylalkyl, alkylaryl, aryl or heteroatom-containing substituents with the proviso that the heteroatom of said heteroatom-containing substituent is not directly bonded to the phosphorous atom, and each R' can have 4 to 20 carbon atoms, and R" group can have 6 to 30 carbon atoms. The two R' groups may be the same or different. R' and/or R" groups containing alkenes or alkynes could also be envisioned but are less common. The phosphonate is used to treat heat transfer surfaces used heat or cool a petroleum or chemical feedstock at coke-forming conditions of 400°–1100° C. The heat transfer surfaces are contacted with an effective amount of a phosphonate.

The heat transfer surfaces can be contacted with the inhibitor in several different ways, including, for example, pretreating the heat transfer surfaces prior to heating or cooling the petroleum feedstock, continuously or intermittently adding a trace amount of the additive to the petroleum feedstock as it is being heated or cooled, adding the phosphonate to steam feed, which is then mixed with the petroleum feedstock, to the petroleum feedstock itself, or to a feed mixture of the petroleum feedstock and steam, among others.

Where the petroleum feedstock being heated or cooled is treated with the phosphonate, the additive is preferably added at a rate from about 0.1 to about 1000 parts per million (ppm) on the basis of elemental phosphorus, more preferably from about 1 to about 100 ppm, by weight of the petroleum feedstock.

For the purposes of this invention, coke formation is defined as any buildup of coke or coke precursors on the heat transfer surfaces, including convection coils, radiant furnace coils, transfer line exchangers, and quench towers, among others. Other phosphorus-containing compounds have been disclosed in various patents and other references as effective coke formation inhibitors. However, none of the phosphorus compounds provide the same performance as the present phosphonate. Performance is based not only on the anticoking agent's ability to suppress and inhibit coke formation, but just as importantly, on being essentially free from causing any harmful side effects associated with many of the previous additives, such as contributing to corrosion or downstream contamination.

As used herein, petroleum feedstock is used to refer to any hydrocarbon generally heated or cooled at the heat transfer surfaces, regardless of the degree of previous processing, and specifically when used in reference to an ethylene or other cracking furnace, refers to the hydrocarbon before processing, as well as the hydrocarbon during and after processing in the furnace itself, in the TLE, in the quench section, etc. The feedstock can include ethane, propane, butane, kerosene, naphtha, gas oil, and combinations thereof.

DESCRIPTION OF THE PREFERRED EMBODIMENTS

Figure 1:
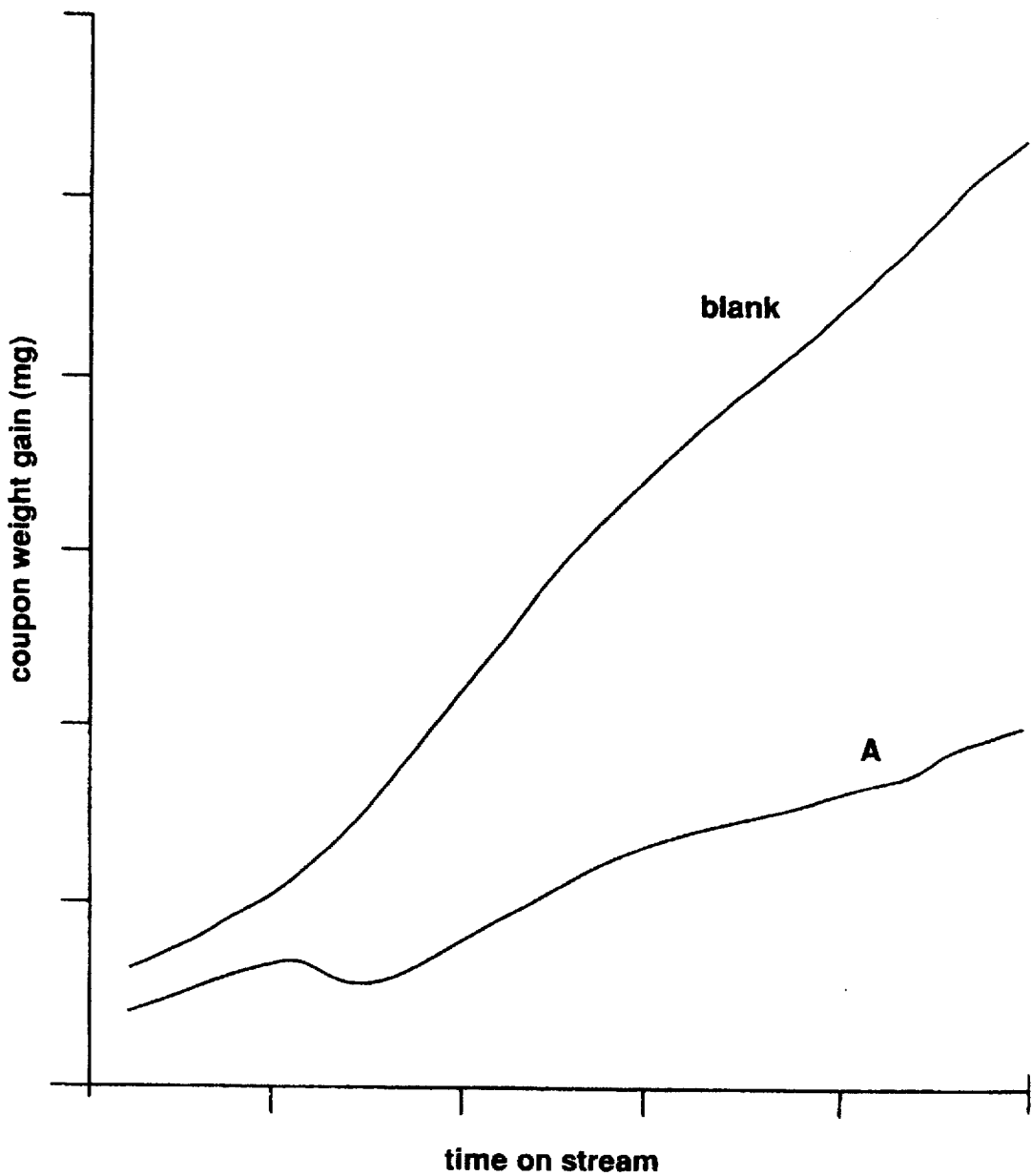
FIG. 1 is a graph illustrating the anticoking performance of a phosphonate, dioctyl phenylphosphonate, in comparison with a blank.

The coking inhibitor of the present invention is a phosphorus compound which is essentially non-corrosive and is essentially free from detrimental by-product formation under general coking conditions.

The present anti-coking agent has the following general formula:

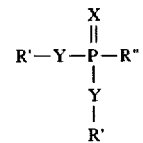

wherein X and Y are chalcogens, preferably oxygen or sulfur, and wherein R'=alkyl or alkylaryl or aryl or arylalkyl or heteroatom-containing substituents with the proviso that the heteroatom of said heteroatom-containing substituent is not directly bonded to the phosphorous atom and R"=alkyl or arylalkyl or aryl or alkylaryl or heteroatom-containing substituents with the proviso that the heteroatom of said heteroatom-containing substituent is not directly bonded to the phosphorous atom, and each R' can have 4 to 20 carbon atoms, and R" group can have 6 to 30 carbon atoms. The two R' groups may be the same or different. R' and/or R" groups containing alkenes or alkynes could also be envisioned but are less common. The phosphonate is used to treat heat transfer surfaces used heat or cool a petroleum or chemical feedstock at coke-forming conditions. The heat transfer surfaces are contacted with an effective amount of a phosphonate. For the purposes of clarity and convenience, and not by way of limitation, the anti-coking agent is referred to herein generally as the preferred phosphonate.

Thus, the invention is a method for inhibiting the formation of coke on heat transfer surfaces in contact with a petroleum feedstock, which feedstocks are at a temperature of from about 400° to about 1100° C. comprising:

contacting said heat transfer surfaces with an effective amount to inhibit coke formation of a phosphonate of the formula $(R'Y)_2P(X)R"$, wherein X and Y are chalcogens selected from the group consisting of oxygen and sulfur, R' is selected from the group consisting of alkyls, alkylaryls, aryls, arylalkyls and heteroatom-containing substituents having 4 to 20 carbon atoms with the proviso that the heteroatom of said heteroatom-containing substituent is not directly bonded to the phosphorous atom and R" is selected from the group consisting of alkyl, arylalkyl, alkylaryl, aryl and heteroatom-containing substituents having 6 to 30 carbon atoms with the proviso that the heteroatom of said heteroatom-containing substituent is not directly bonded to the phosphorous atom.

The fact that there is a preferred lower number of carbon atoms for the R' and R" substituents is mainly due to corrosion concerns. In general, the more robust or bulky the R' and R" substituents in a phosphonate are, the more hydrophobic the phosphonate. In turn, the phosphonate is less likely to form corrosive media by hydrolysis, and thus possesses lower corrosion potential.

Moreover, if the number of carbon atoms in the phosphonate is excessively large, the economics of the additive are less favorable, the additive can lose volatility and miscibility in the petroleum feedstock being treated, or can lose stability. The hydrocarbon groups can be substituted with or contain a heteroatom such as a chalcogen, Group VA element or others, but this is generally less preferred because of the instability imparted by the heteroatom. In some situations, the presence of a heteroatom can be useful, especially where the heteroatom is in a terminal portion of the hydrocarbon group spaced from the phosphonate moiety, so that any cleavage or other reaction of the heteroatom will leave the phosphonate moiety substantially intact for anti-coking effectiveness. Examples of such useful heteroatom-containing substituents are amines, sulfides, ethers and thioethers. The term phosphonate as utilized herein describes phosphorous-containing compounds with one phosphorus to carbon bond, represented herein by the R" functional group.

The phosphonate is used to inhibit coke formation on heat transfer surfaces, by treating the surfaces with an effective amount of the phosphonate. The surface can be effectively treated, for example, by introducing the phosphonate into the petroleum feedstock before the feedstock comes into contact with the heat transfer surfaces.

In general, the phosphonate can be used in an amount effective to obtain the desired inhibition of coke formation, usually at least 0.1 ppm by weight in the hydrocarbon, preferably at least 1 ppm, on the basis of elemental phosphorus. There is usually no added benefit in using the phosphonate in a relatively high concentration, and the economics are less favorable. Preferably, the phosphonate is used in an amount from about 0.1 to about 1000 ppm, more preferably from about 1 to about 100 ppm, by weight in the hydrocarbon, on an elemental phosphorus basis.

The addition to the petroleum feedstock is preferably continuous, but it is also possible to use the petroleum feedstock treatment on an intermittent basis, depending on the coke inhibition which is desired in the particular application. For example, where there is a scheduled shutdown of the heat transfer equipment for maintenance, other than for the build up of coke deposits, the continuous addition of the phosphonate to the petroleum feedstock could be terminated in advance of the shutdown. Alternatively, the anti-coking agent could be used in the petroleum feedstock after the development of a pressure drop indicative of coke formation therein through the heat transfer equipment.

It is also possible to treat the heat transfer surfaces before they come into contact with the petroleum feedstock, by applying the phosphonate as a pretreatment or as a treatment between production runs. As a pretreatment, the phosphonate can be circulated through the heat transfer equipment, preferably in a suitable diluent. The heat transfer equipment can also be filled with the phosphonate solution and allowed to soak for a period of time to form a protective barrier on the heat transfer surfaces. For an alternative pre-treatment method, the phosphonate can be painted or sprayed onto the heat transfer surfaces. Similarly, the petroleum feedstock can be dosed at a relatively high initial rate, e.g. 0.05 to 2.0 weight percent, and after a period of time, e.g. 1 to 24 hours, reduced to the continuous dosage rates described above.

Where the petroleum feedstock being heated or cooled is being treated on a generally continuous basis, the phosphonate is preferably added as a solution in a master batch. The mode of blending the phosphonate with the feedstock is not particularly critical, and a vessel with an agitator is all that is required. However, most conveniently, a master batch of the phosphonate, in a suitable solvent, such as aliphatic or aromatic hydrocarbon, is metered into a stream of the feedstock and intimately mixed therein by turbulence in the processing equipment. The phosphonate may also be used neat instead of diluting with a solvent. Also, the phosphonate can be added to a steam or water stream which is injected or otherwise added to the petroleum feedstock stream, or the phosphonate can be added to a mixed stream of the petroleum feedstock and steam or water.

The phosphonate should be added to the feedstock upstream of the heat transfer surfaces being treated. The phosphonate addition should be sufficiently upstream to allow sufficient mixing and dispersion of the additive in the feedstock, but preferably not too far upstream so as to avoid or minimize any significant decomposition or degradation of the phosphonate.

The invention is illustrated by way of the following examples. These examples are presented to describe preferred embodiments and utilities of the invention and are not meant to limit the invention unless otherwise stated in the claims appended hereto.

EXAMPLE 1

In the following examples, various phosphorus compounds were evaluated and compared for coke inhibition, corrosivity and by-product formation. The additives used are designated as indicated in Table 1.

TABLE 1

Active Phosphorus Components in Additives

| ADDITIVE | ACTIVE COMPONENT |
|---|---|
| A | Dioctyl phenylphosphonate |
| B | Diethyl benzylphosphonate |
| C | Dibutyl butylphosphonate |
| D | Amine-neutralized phosphate mono/diester* |
| E | Amine-neutralized thiophosphate mono/diester* |
| F | Triphenylphosphine |
| G | Borane-tributylphosphine complex |

*Alkyl groups were $C_6$–$C_{10}$ paraffins; neutralized with morpholine.

All weights and percentages are on a weight basis unless otherwise indicated.

For coke suppression data, a laboratory reactor was used to duplicate conditions in an ethylene furnace as closely as possible. Coke formation was measured on a coupon constructed of Incoloy 800 alloy placed in the lab reactor.

Experimental conditions used to evaluate a phosphonate were as follows. The additives were precoated on test coupons through a dipping technique. First, a metal coupon was soaked with the additive solution (i.e. active component in heavy aromatic naphtha) at an elevated temperature for several hours, and then dried at room temperature in air. The coupons were made of Incoloy 800 and were of a dimension of 2"×0.25"×0.065". The coupons were first subjected to flowing argon at room temperature and then a mixture of steam and argon with elevating temperature. The cracking reactions were initiated by introducing heptane into the process stream at a temperature of ca. 780° C. The cracking operation typically lasted for about 2 hours. The heptane and steam feeding rates were maintained constant and at a weight ratio of 3:1 during a run. During this time period, the coupon weight gain, an indication of coke buildup, was continuously recorded using an electronic microbalance equipped with a computer data acquisition system. The coking rate was determined from the slope of the curve in a plot of coupon weight gain vs. time on stream. The steeper the slope is, the higher the coking rate. Product anticoking performance was compared to the cracking runs in which coupons were coated with solvent containing no additive (i.e. a blank).

Figure 2:
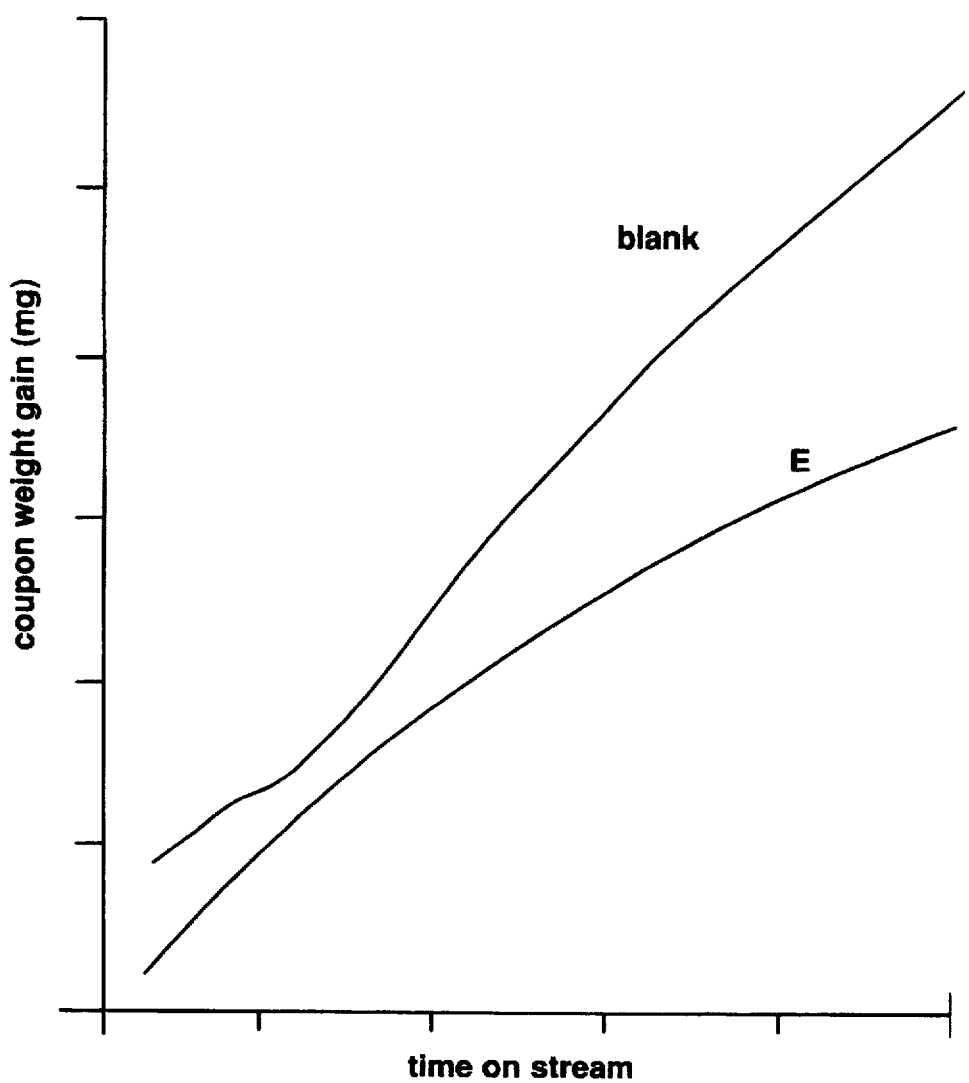
FIG. 2 compares an amine-neutralized thiophosphate mono/diester with a blank.

FIG. 1 illustrates the additive's ability to reduce the coking rate with respect to the blank run performed under identical conditions. This performance is comparable or better than the performance of other phosphorus containing additives such as those described in U.S. Pat. No. 4,842,716 (See FIG. 2 for additive E).

EXAMPLE 2

A high temperature wheel box was used to determine the degradation-corrosion properties of various additives over long periods of time. To accelerate corrosion effects. Additive A was used at a concentration of 15 percent in toluene and the other additives were used at an equivalent phosphorus content. The additive was added to a high alloy vessel along with hydrocarbon, varying amounts of water and preweighted coupons constructed of carbon steel. The contents were rotated continuously at temperatures representative of a typical convection section of an ethylene furnace. The mixing ensured that the coupons would be exposed to both a liquid and a gas phase (composed of water and hydrocarbon). Exposing the additives to high temperature for extended periods of time permitted potential decomposition to harmful by-products. In essence, this method simulated a worst case scenario involving a fairly high concentration of an additive in the convection section with eventual accumulation/degradation (e.g. thermolysis, hydrolysis, disproportionation, etc.) to by-products which may or may not be corrosive. Additionally, the appearance of corrosion may not be the direct result of degradation, but may be an inherent property of an additive. In Table 2, test data for Additive A is compared against other compounds, one of which was an amine-neutralized phosphate ester mono- and di-substituted with alkyl groups, a known coke suppressant with aggressive corrosivity. As can be seen, the dioctyl phenylphosphonate (A) exhibited excellent performance. The same was not true for the other phosphorus compounds.

TABLE 2

| High Temperature Wheel Box Corrosion Test Results | |
|---|---|
| ADDITIVE | WEIGHT LOSS (mg) |
| blank | 2.5 |
| A | 6.5 |
| B | 26.6 |
| C | 53.0 |
| D | 134 |

EXAMPLE 3

A lab unit was constructed which would simulate the dynamic (i.e. erosion-corrosion) conditions of a typical convection section of an ethylene furnace. Corrosion is more likely to occur at or near the bends/elbows of the convection sections because of high erosion due to the velocity of the stream. Steam, generated from one vessel, was mixed with hydrocarbon (hexane and toluene at 50—50 weight percent) from a second vessel (steam:hydrocarbon weight ratio 0.5–0.6). Heating to the desired temperature was accomplished by passing the mixture through two independent furnaces at specified temperatures (100°–600° C.). Both furnaces were monitored and controlled via two separate temperature controllers. Preweighted corrosion coupons, made of carbon steel, were situated at a bend within the furnace coil. Coupon A was situated in the process flow and subjected to the erosive and corrosive nature of the process stream. Coupon B was situated in a dead-leg projecting out of the bend of interest. This positioning permitted the accumulation of corrosive species, but shielded Coupon B from the nearby erosive environment. In essence, Coupon B was situated to study the effects of points where the process flow was extremely dormant (i.e. non-turbulent areas). Thermocouples were used to record the temperature of the coupons as well as both furnace sections.

The additives were introduced to the hydrocarbon feed and tested under conditions identical to a blank (without additive). Coupon weight loss for several additives is given in Table 3. Dioctyl phenylphosphonate (A), at 2.4 weight percent in the hydrocarbon, gave excellent results compared to additive E, a known erosive and corrosive past product, at an equivalent phosphorus content.

TABLE 3

| Dynamic Flow Corrosion Test Results | | |
|---|---|---|
| | WEIGHT CHANGE (mg) | |
| ADDITIVE | COUPON A | COUPON B |
| blank | +0.1 | −0.1 |
| A | −0.3 | +0.1 |
| E | −28.3 | −1.0 |

EXAMPLE 4

To determine the propensity of various phosphorus-based products to yield phosphine, $PH_3$, a known detrimental by-product, additives were evaluated in the apparatus described in the Example 3. Additive A was used at 7.4 weight percent in the hydrocarbon, and all other additives were used at an equivalent phosphorus content. To achieve the proper cracking temperature, a radiant section (750°–950° C.) was added just after the convection section. To more accurately simulate a typical ethylene furnace downstream quenching process, the effluent gases were passed through several vessels maintained at low temperatures (0° C. and −78° C.), a caustic scrubber, and a dryer containing 3 Å molecular sieves. Phosphine production levels given in Table 4 below are relative to each other (Additive F reading=100) and were determined by the calorimetric reading taken from a gas detector situated downstream from all the condensers. A low value indicates little $PH_3$ was produced while high values indicate large levels were produced.

TABLE 4

| Relative Phosphine Formation Rates | |
|---|---|
| ADDITIVE | RELATIVE $PH_3$ FORMATION RATE |
| A | <0.4* |
| D | <0.4* |
| F | 100 |
| G | 250 |

*below detection limit

From the foregoing data, it is seen that the dioctyl phenylphosphonate evaluated is as effective in coke suppression as the known phosphorus-based additives, but is essentially free from contributing to corrosion and from forming phosphine. It is further seen that the other phosphorus-based additives evaluated either contributed to corrosion or formed phosphine under coking conditions.

Changes can be made in the composition, operation and arrangement of the method of the present invention described herein without departing from the concept and scope of the invention as defined in the following claims:

We claim:

1. A method for inhibiting the formation of coke on heat transfer surfaces in contact with petroleum feedstocks, which feedstocks are at a temperature of from about 400° to about 1100° C. comprising:

contacting said heat transfer surfaces with an effective amount to inhibit coke formation of a phosphonate of the formula $(R'Y)_2P(X)R''$, wherein X and Y are chalcogens selected from the group consisting of oxygen and sulfur, R' is selected from the group consisting of alkyls, alkylaryls, aryls, arylalkyls and heteroatom-containing substituents having 4 to 20 carbon atoms with the proviso that the heteroatom of said heteroatom-containing substituent is not directly bonded to the phosphorous atom and R" is selected from the group consisting of alkyl, arylalkyl, alkylaryl, aryl and heteroatom-containing substituents having 6 to 30 carbon atoms with the proviso that the heteroatom of said heteroatom-containing substituent is not directly bonded to the phosphorous atom.

2. The method of claim 1 wherein the heteroatom-containing substituents for R' and R" heteroatoms are selected from the group consisting of oxygen, sulfur and nitrogen.

3. The method of claim 2 wherein the phosphonate comprises dioctyl phenyl-phosphonate.

4. The method of claim 1 wherein the heteroatom-containing substituents for R' and R" are selected from the group consisting of ethers, thioethers, amines and sulfides.

5. The method of claim 1, wherein the petroleum feedstocks being heated or cooled are treated with from 0.1 to 1000 parts per million of phosphonate on the basis of elemental phosphorus in the phosphonate by weight of the feedstock.

6. The method of claim 1, wherein the petroleum feedstocks being heated or cooled are treated with from 1 to 100 parts per million of phosphonate on the basis of elemental phosphorus in the phosphonate by weight of the feedstock.

7. The method of claim 1, wherein the petroleum feedstock is selected from the group consisting of ethane, propane, butane, naphtha, kerosene, gas oil and combinations thereof.

8. The method of claim 1, wherein the heat transfer surfaces are selected from the group consisting of cracking furnace coils and transfer line exchangers.

9. The method of claim 1, wherein the heat transfer surfaces are pretreated with the phosphonate before processing the petroleum feedstock.

10. The method of claim 1 wherein the phosphonate is applied to the heat transfer surface by a method selected from the group consisting of spraying, soaking and painting.

11. The method of claim 1, further comprising:

adding the phosphonate continuously or intermittently to a petroleum feedstock;

and passing the resulting admixture through convection and radiant sections of a cracking furnace.

12. The method of claim 1, further comprising:

adding the phosphonate continuously or intermittently to steam;

mixing the steam with a petroleum feedstock; and passing the admixture of feedstock and steam containing the phosphonate through a cracking furnace.

13. The method of claim 1, further comprising:

adding the phosphonate continuously or intermittently to a mixture of steam and a petroleum feedstock; and passing the resulting admixture through a cracking furnace.

14. The method of claim 2, wherein the phosphonate causes no detrimental side effects, such as corrosion and downstream contamination.

* * * * *